US011000412B2

(12) United States Patent
Nobis et al.

(10) Patent No.: US 11,000,412 B2
(45) Date of Patent: May 11, 2021

(54) SYSTEM FOR THERAPY OF THE EYE BY TREATING TISSUE USING NON-LINEAR INTERACTION

(71) Applicant: Carl Zeiss Meditec AG, Jena (DE)

(72) Inventors: Thomas Nobis, Jena (DE); Marco Hanft, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/318,448

(22) PCT Filed: Jul. 17, 2017

(86) PCT No.: PCT/EP2017/068044
§ 371 (c)(1),
(2) Date: Jan. 17, 2019

(87) PCT Pub. No.: WO2018/015349
PCT Pub. Date: Jan. 25, 2018

(65) Prior Publication Data
US 2019/0290483 A1 Sep. 26, 2019

(30) Foreign Application Priority Data

Jul. 18, 2016 (DE) .......................... 102016213095.1
Apr. 12, 2017 (DE) .......................... 102017107915.7

(51) Int. Cl.
*A61F 9/008* (2006.01)
(52) U.S. Cl.
CPC .......... *A61F 9/008* (2013.01); *A61F 9/00825* (2013.01); *A61F 2009/0087* (2013.01);
(Continued)

(58) Field of Classification Search
CPC .................. A61F 9/008; A61F 9/00825; A61F 2009/0087; A61F 2009/00872; A61F 2009/00897
See application file for complete search history.

(56) References Cited

U.S. PATENT DOCUMENTS 5,246,435 A 9/1993 Bille et al.
6,325,792 B1 12/2001 Swinger et al.
(Continued)

FOREIGN PATENT DOCUMENTS

CA 2 772 138 A1 6/2011
CN 102481205 A 5/2012
(Continued)

*Primary Examiner* — Michael W Kahelin
*Assistant Examiner* — George E Banis
(74) *Attorney, Agent, or Firm* — Christensen, Fonder, Dardi & Herbert PLLC

(57) ABSTRACT

A system for therapy of the eye by treating tissue with therapeutic radiation using nonlinear interaction. A laser device is provided, which delivers the therapeutic radiation. The therapeutic radiation is focussed by a focussing device in an image field, and xy scanners and z scanners shift the focus laterally and longitudinally within a treatment volume. The therapeutic radiation is either a second short pulse radiation or a first short pulse radiation, each of which have a spectral centroid within a wavelength range defined by the short pulse properties. The system is particularly corrected with regard to longitudinal chromatic aberrations and lateral chromatic aberrations such that the spectral characteristic curves of the two aberrations each have a local extreme within the wavelength ranges, and a certain tolerance within the wavelength ranges is not exceeded, therefore the characteristic curves are very shallow.

20 Claims, 5 Drawing Sheets

(52) U.S. Cl.
CPC ............... *A61F 2009/00872* (2013.01); *A61F 2009/00887* (2013.01); *A61F 2009/00889* (2013.01); *A61F 2009/00897* (2013.01)

(56) References Cited

U.S. PATENT DOCUMENTS

| | | | |
|---|---|---|---|
| 9,110,301 B2* | 8/2015 | Lippert | ................ G02B 21/002 |
| 2005/0085800 A1 | 4/2005 | Lenzner et al. | |
| 2006/0012785 A1 | 1/2006 | Funk et al. | |
| 2006/0195076 A1 | 8/2006 | Blumenkranz et al. | |
| 2009/0131921 A1 | 5/2009 | Kurtz et al. | |
| 2011/0116040 A1 | 5/2011 | Biernat et al. | |
| 2011/0118713 A1 | 5/2011 | Raksi | |
| 2012/0310223 A1* | 12/2012 | Knox | ................ A61F 9/00834 606/5 |
| 2014/0228826 A1* | 8/2014 | Blumenkranz | ...... A61B 90/361 606/6 |
| 2014/0257259 A1 | 9/2014 | Papastathopoulos et al. | |
| 2014/0288540 A1 | 9/2014 | Bischoff et al. | |
| 2014/0307242 A1* | 10/2014 | Solak | ................ G03F 7/70408 355/67 |
| 2015/0208915 A1* | 7/2015 | Schallek | ................ A61B 3/14 351/206 |
| 2015/0272782 A1* | 10/2015 | Schuele | ............... A61B 3/1173 606/5 |
| 2015/0323774 A1* | 11/2015 | Lippert | ................ G02B 21/002 359/388 |
| 2015/0366711 A1* | 12/2015 | Bischoff | .................. A61F 9/008 606/5 |
| 2016/0045364 A1 | 2/2016 | Raksi et al. | |
| 2016/0095752 A1* | 4/2016 | Srinivasan | .......... A61F 9/00834 606/6 |
| 2016/0131900 A1* | 5/2016 | Pretorius | ............ G02B 13/0095 359/368 |
| 2016/0216499 A1 | 7/2016 | Nobis | |
| 2016/0259163 A1 | 9/2016 | Hoegele et al. | |

FOREIGN PATENT DOCUMENTS

| | | |
|---|---|---|
| DE | 10 2004 034 977 A1 | 2/2006 |
| DE | 10 2008 011 836 A1 | 9/2009 |
| DE | 10 2011 085 046 A1 | 4/2013 |
| DE | 10 2015 201 393 A1 | 7/2016 |
| DE | 10 2015 203 844 A1 | 9/2016 |
| EP | 1 792 593 A1 | 6/2007 |
| WO | WO 03/057100 A2 | 7/2003 |
| WO | WO 2007/124602 A1 | 11/2007 |
| WO | WO 2008/077532 A1 | 7/2008 |
| WO | WO 2011/059958 A2 | 5/2011 |

* cited by examiner

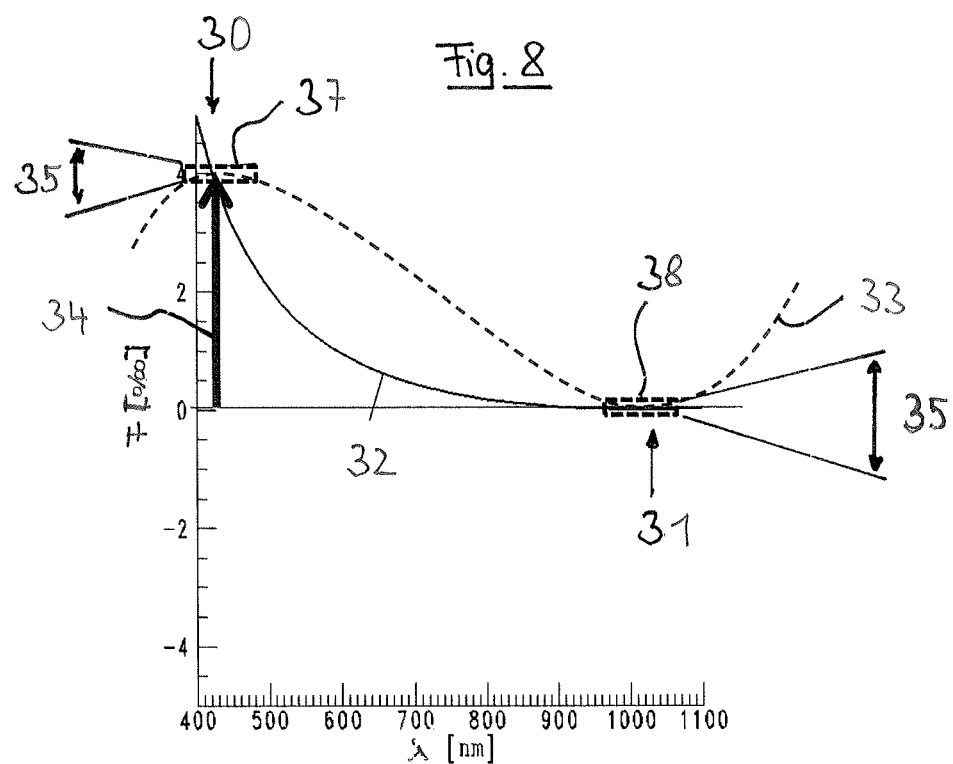

SYSTEM FOR THERAPY OF THE EYE BY TREATING TISSUE USING NON-LINEAR INTERACTION

PRIORITY CLAIM

The present application is a National Phase entry of PCT Application No. PCT/EP2017/068044, filed Jul. 17, 2017, which claims priority from German Patent Application No. 10 2016 213 095.1, filed Jul. 18, 2016, and German Patent Application No. 10 2017 107 915.7, filed Apr. 12, 2017, the disclosures of which are hereby incorporated by reference herein in their entirety.

FIELD OF THE INVENTION

The invention relates to a system or measurement for therapy of the eye by treating tissue by means of nonlinear interaction with therapy or measurement radiation, the system comprising: a laser device, which provides the therapy or measurement radiation, a focusing device, which comprises an image field lying in a therapy or measurement volume and which focuses the therapy radiation onto a focus in the image field such that the treatment or measurement is producible within the tissue by means of nonlinear interaction, an xy-scanner device, disposed upstream of the focusing device, for lateral displacement of the focus in the image field, a z-scanner device, which adjusts a depth position of the focus in the therapy volume, and a control device, which controls the xy-scanner and the z-scanner.

BACKGROUND OF THE INVENTION

Examples for the application of systems for therapy of the eye are the laser-assisted refractive eye surgery or the laser-assisted cataract operation. In refractive eye surgery, cut surfaces, which isolate a volume and render the latter removable, are produced within the cornea by means of laser radiation. The volume is dimensioned such that its removal changes the corneal curvature such that a refractive error that previously existed is compensated. In the cataract operation, the natural lens of the eye, which has turned opaque, is replaced by an artificial intraocular lens (IOL). To this end, a hole is cut in the front side of the capsular bag of the lens of the eye. After a preceding fragmentation, the lens is removed through this hole and an artificial intraocular lens (IOL) is inserted. A cut is introduced into the cornea and/or sclera for the necessary access to the anterior chamber. Additionally, incisions, e.g., arcuate cuts, are possible on the cornea for the purposes of reducing a corneal astigmatism. Full or partial removal of the rear-side capsular bag may be required post surgery in the case of a so-called "secondary cataract". Here, the term "capsulotomy" is used for the introduction of cuts into the capsular bag (on the anterior and/or posterior side thereof). Here, short-pulse lasers are used, for example in order to "cut" eye tissue by means of photodisruption.

In order to obtain a treatment effect within a tissue by means of laser radiation, the laser radiation must also develop its interaction in the interior of the tissue. Therefore, laser radiation for which the tissue actually appears transparent is used in ophthalmology and an energy density that triggers a treatment effect is produced in a spatially strongly restricted focus. An optical breakdown, which is also referred to as photodisruption in the literature, often arises in the process. Usually, use is made of short-pulse laser radiation that is focused onto a tight focus. The focal dimension is an essential parameter. This also applies to the depth position and the depth extent of the focus. In conventional ablation techniques, both parameters have no relevance since said techniques carry out a layer-by-layer ablation at the surface of the material, i.e., do not act within the material.

U.S. Pat. No. 6,325,792 B1 proposes that pulses of a femtosecond laser are focused into the lens of the eye in order to cut open the capsular bag. U.S. Pat. No. 5,246,435 discloses the focusing of pulses of a short-pulse laser into the natural lens of the eye with a three-dimensional cut pattern in order to fragment the lens into fragments by the cuts and the subsequent bubble formation, and thereby liquefy the latter.

For the purposes of deflecting the femtosecond pulses, use is made, firstly, of stationary objectives and fast mirror scanners for the lateral x/y-deflection of the laser beam in the eye and slowly adjustable lenses for the z-deflection of the focal position along an optical axis of the eye. For instance, such systems are described in US 2006/195076 A1 or US 2009/131921 A1. Secondly, systems in which the objective is moved slowly in the lateral direction are also known, wherein use is made of a fast-moving lens for the z-deflection of the focus along the optical axis of the eye. Such a system carries out a so-called objective scan and is described in DE 102011085046 A1, for example.

Within the scope of therapy of the eye by way of focused pulses of a femtosecond laser, the focus must be imaged sharply over a certain depth adjustment range. In applications on the cornea of the eye, between 0.5 and 2 mm of focus travel have to be realized. In the application both on the lens of the eye and on the cornea, a focus travel of up to 15 mm is required.

Operation at two different wavelengths is desirable for many optical applications. For the purposes of treating tissue by nonlinear interaction with therapy radiation or for the purposes of observing eyes, applications with femtosecond pulses in either the infrared or the ultraviolet are known in eye care. In order to obtain an energy density required for nonlinear interaction or for high observation quality, primary chromatic aberrations (longitudinal chromatic aberration and the transverse chromatic aberration) must be corrected properly. Due to the short-pulse nature of radiation, correction is required not only for the centroid wavelength but also for a wavelength range that comes from the short-pulse nature. The edges of this wavelength range represent secondary wavelengths at which a good correction of the chromatic aberrations is still required. If chromatic aberrations are not removed, the fs-pulses are broadened when passing through optics and a power density in the focal volume that is required for a given application is not reached. In applications utilizing UV radiation, the centroid wavelength is 405 nm, for example, and the wavelength range extends from 400 nm to 410 nm. Conventional achromatization of a system at two wavelengths—i.e., for example, the secondary wavelengths 400 nm and 410 nm—leads to strong residual aberrations for wavelengths away from this spectral range (that is to say, e.g., at 1030 nm to 1050 nm). These residual aberrations come from characteristic dispersion of available technical glasses. Under certain circumstances, longitudinal chromatic aberrations and transverse chromatic aberrations can be corrected for a further wavelength (e.g., the first mid-wavelength of 1040 nm) by the use of so-called exotic special-purpose glasses with abnormal dispersion. Then, a correction is required at four wavelengths (superapochromatic correction), namely at 400 nm, 410 nm, 1030 nm and 1050 nm. In theory, this is theoretically possible by computing a complicated glass selection but implementable in practice with very high technical outlay only. The fact that both longitudinal and transverse chromatic aberrations have to be corrected simultaneously for the four wavelengths is also an obstacle to such conventional solution. In certain system sections, use of special-purpose glasses generates to a corrective effect for both aberrations; i.e., an employed special-purpose glass has a positive effect on both longitudinal and transverse chromatic aberration. However, after an intermediate image or after a pupil plane, the effect on the transverse chromatic aberration reverses, and so, up to the next intermediate image or up to the next pupil plane, the employed special-purpose glasses disturb the correction for one of the two aberrations. This leads to further complications if the corrective effect has already been used up in the first-mentioned system section. An alternative solution to the problem would lie in a replacement of the entire optical system (pivoting optical unit) if the operation at the different wavelength ranges needs not to be implemented simultaneously. This demands much outlay in terms of mechanisms and optical units.

Particularly in the case of scanning systems, which laterally displace the focus within an image field, transverse chromatic aberrations are particularly bothersome as they depend on the image height which is caused by the lateral deflection of the scanner in a scanning system.

SUMMARY OF THE INVENTION

Therefore, the invention is based on the object of configuring a system of the type set forth at the outset such that treatment by nonlinear interaction within a tissue is possible in the case of two centroid wavelengths that have a comparatively large distance therebetween.

The system is configured for therapy of the eye, wherein tissue is treated by nonlinear interaction with therapy radiation. A laser device provides therapy radiation. A focusing device comprises an image field situated in a therapy volume and focuses the therapy radiation to a focus in the image field. The focus and the laser device are configured such that the treatment within the tissue is effected by nonlinear interaction. A xy-scanner device is disposed upstream of the focusing device. It displaces the focus laterally in the image field. Further, the system comprises a z-scanner device, which adjusts a depth position of the focus in the therapy volume. The xy-scanner and z-scanner are controlled by a control device. The laser device provides the therapy radiation. A first short-pulse radiation lies at a first centroid wavelength. A second short-pulse radiation lies at a second centroid wavelength, which differs from the first centroid wavelength by at least 300 nm, preferably 500 nm. Due to the pulse length, in particular in a pulse length range between 1 ps and 1 fs, the two short-pulse radiations each cover a wavelength range that includes the respective centroid wavelength. The system has at least two swithable modes of operation. It operates with the first short-pulse radiation in a first mode of operation and with the second short-pulse radiation in a second mode of operation. In respect of longitudinal chromatic aberration and transverse chromatic aberration, it is configured such that the system has a longitudinal chromatic aberration at at least one of the two centroid wavelengths. In the first and in the second wavelength range, a spectral characteristic curve of the longitudinal chromatic aberration extends substantially horizontally. The curve is constant within a longitudinal chromatic aberration tolerance. Further, in respect of the transverse chromatic aberration, the system is configured such that the focusing device exhibits a transverse chromatic aberration at at least one of the two centroid wavelengths. In both wavelength ranges, a spectral characteristic curve of the transverse chromatic aberration is constant within a transverse chromatic aberration tolerance. Thus, the characteristic curve has a substantially horizontal section in both wavelength ranges. The control device is configured to control the xy-scanner device such that the transverse chromatic aberration is compensated by a suitably adapted deflection function for the lateral displacement of the focus.

However, the system may also be configured for examination. Then, the therapy radiation constitutes examination radiation or measurement radiation; the therapy volume is an examination volume. Here, the examination can be implemented by means of nonlinear interaction, for example multi-photon processes. This is not mandatory, however. All that is decisive for such a modification of the system is that wavelength ranges, within which the longitudinal chromatic aberration and transverse chromatic aberration are constant within the aforementioned tolerances, are caused for the first and second short-pulse radiation as a result of the short-pulse nature of the radiation, in particular in a pulse length range between 1 ps and 1 fs.

The laser device, which provides the therapy radiation, is provided in the system for therapy of the eye by treating tissue by means of nonlinear interaction with therapy radiation. The therapy radiation is focused in the image field by the focusing device, and xy-scanner and z-scanner displace the focus laterally and in a depth direction in a therapy volume. As a result of the short-pulse properties, the therapy radiation covers a wavelength range. In respect of longitudinal chromatic aberrations and transverse chromatic aberrations, the system is particularly well-corrected, and so the spectral characteristic curves of both aberrations each have a local extremum in the wavelength ranges, with a certain tolerance not being exceeded in the wavelength ranges; i.e., the characteristic curves are very flat.

The longitudinal chromatic aberration or the spectral characteristic curve associated therewith describes the axial variation of the focal position as a function of the wavelength. The longitudinal chromatic aberration is specified in relation to the axial focal position of a reference wavelength, for example—but not necessarily—in relation to the first or the second centroid wavelength. Then, the longitudinal chromatic aberration of the reference wavelength equals zero by definition; the characteristic curve has a zero.

The system has a longitudinal chromatic aberration at at least one of the centroid wavelengths. If one of the two centroid wavelengths is taken as reference wavelength for the longitudinal chromatic aberration, the longitudinal chromatic aberration occurs at the respective other of the two centroid wavelengths. If neither of the two centroid wavelengths is the reference wavelength for the longitudinal chromatic aberration, the system exhibits a longitudinal chromatic aberration at both centroid wavelengths. The flatness of the characteristic curve within the longitudinal chromatic aberration tolerance has as a consequence that the system has no longitudinal chromatic aberration within the first wavelength range if a wavelength from this wavelength range is chosen as reference wavelength, e.g., the first centroid wavelength. The same applies to the second wavelength range if a wavelength from this wavelength range is chosen as reference wavelength.

An analogous situation occurs for the transverse chromatic aberration. The transverse chromatic aberration or the spectral characteristic curve associated therewith describes the lateral variation of the focal position transversely to the optical axis or to the direction of light propagation, as a function of the wavelength. The transverse chromatic aberration is specified in relation to the lateral focal position of a reference wavelength, for example—but not necessarily—in relation to the first or the second centroid wavelength. Then, the longitudinal chromatic aberration of the reference wavelength equals zero by definition; the characteristic curve has a zero.

The system has a transverse chromatic aberration at at least one of the centroid wavelengths. If one of the two centroid wavelengths is taken as reference wavelength for the transverse chromatic aberration, the transverse chromatic aberration occurs at the respective other of the two centroid wavelengths. If neither of the two centroid wavelengths is the reference wavelength for the transverse chromatic aberration, the system exhibits a transverse chromatic aberration at both centroid wavelengths. The flatness of the characteristic curve within the transverse chromatic aberration tolerance has as a consequence that the system has no transverse chromatic aberration within the first wavelength range if a wavelength from this wavelength range is chosen as reference wavelength, e.g., the first centroid wavelength. The same applies to the second wavelength range if a wavelength from this wavelength range is chosen as reference wavelength.

The aberration tolerances allow the corresponding longitudinal chromatic aberration or transverse chromatic aberration to still have a minor variation within the aforementioned wavelength ranges; i.e., the volume covered by the focus of the short-pulse radiation is axially widened in the case of the longitudinal chromatic aberration and laterally widened in the case of the transverse chromatic aberration. Here, the term "minor" is dimensioned such that the widening does not destroy the conditions for the effect of the short-pulse radiation, i.e., for producing nonlinear interaction or the desired observation quality. Expressed differently, the longitudinal chromatic aberration tolerance is dimensioned such that the axial widening of the focal volume of the short-pulse radiation remains restricted to such an extent that the production of nonlinear interaction is not impaired or not inadmissibly impaired. The same applies in the lateral direction to the transverse chromatic aberration. In embodiments, the longitudinal chromatic aberration tolerance is, e.g., a certain multiple of the depth of field, for example $0.1\times$, $0.2\times$, $0.5\times$, $1\times$ or $2\times$ the depth of field of the focusing device. In other embodiments, combinable therewith, the transverse chromatic aberration tolerance is a certain multiple of the lateral focal dimension in relation to the so-called Airy diameter, for example $0.1\times$, $0.2\times$, $0.5\times$, $1\times$ or $2\times$ the Airy diameter. This constancy of the characteristic curve is therefore required since the short-pulse radiations cover the wavelength range about the respective centroid wavelength due to the short-pulse nature. This cannot be prevented. In the case of a centroid wavelength of 405 nm, the wavelength range has a width of 10 nm, for example. Should the centroid wavelength be 1040 nm, it has a width of 20 nm, for example. The constancy of transverse chromatic aberration and of longitudinal chromatic aberration within the corresponding tolerance ensures that the wavelength ranges are guided in the system, and in particular by the focusing device, such that their range width does not lead to a widening of the focal volume that would be so large that nonlinear interaction is no longer achieved or the latter is no longer achieved to a sufficient extent or that a desired observation quality would be missed.

As a result of the requirements on the spectral characteristic curves, the system can dispense with an apochromatization of the optics. The remaining (albeit constant) transverse chromatic aberration at at least one of the centroid wavelengths leads to a deflection angle adjusted by the xy-scanner device gets an additional or reduced lateral deflection in the therapy volume due to the transverse chromatic aberration. Since the transverse chromatic aberration is known, the control device ensures that this extra lateral displacement of the focus is compensated by an appropriate adapted actuation of the xy-scanner device. Thus, a complicated correction is replaced in surprisingly simple fashion by an adapted actuation of the xy-scanner device.

The longitudinal chromatic aberration that exists between the second and the first centroid wavelength likewise can be compensated by the control device by virtue of the latter actuating the z-scanner device such that, during operation with the short-pulse radiation affected by the longitudinal chromatic aberration, the depth position of the focus is compensated by an appropriate adapted offset. Of course, due to the demanded constancy of the spectral characteristic curve of the longitudinal chromatic aberration, the longitudinal chromatic aberration generates a simple offset in depth position of the focus but no inadmissible axial focal deformation for the first wavelength range.

As an alternative or in addition to the corresponding compensation of the longitudinal chromatic aberration by the z-scanner device, it is possible to use a refocusing element that only acts on the short-pulse radiation that is affected by the aberration or that is only activated in said case, said refocusing element partly compensating or fully compensating the longitudinal chromatic aberration by an appropriate offset in the depth position of the focus.

The alternating operation of the system with the two short-pulse radiations, i.e., the modes of operation specified above, can be realized with little outlay in embodiments by virtue of the system comprising a first input beam path for the first short-pulse radiation and a second input beam path for the second short-pulse radiation and further comprising a beam combiner disposed upstream of the focusing device, said beam combiner merging the two input beam paths or switching between these two input beam paths. In this way, it is possible to provide the corrections for the longitudinal chromatic aberration in the respective individual input beam paths or, and this is preferable, it is possible to correct the first input beam path or the focusing device such that the spectral characteristic curve of the longitudinal chromatic aberration is constant within the aforementioned longitudinal chromatic aberration tolerance in this wavelength range. Then, a correction member controlled by the control device is arranged in the beam path downstream of the beam combiner in embodiments, said correction member being activatable in respect of a corrective effect for the second wavelength range. In the case the corrective effect is active, the correction member modifies the optical path such that in the second wavelength range the spectral characteristic curve of the longitudinal chromatic aberration that is constant within the longitudinal chromatic aberration tolerance is provided. The control device activates the correction member in respect of the corrective effect thereof only if the second short-pulse radiation passes through the system. It deactivates the correction member in respect of its corrective effect when the first short-pulse radiation passes through the system since the system is already corrected for this radiation. Optics that already have an ideal color correction for the first short-pulse radiation can thus be extended with little outlay for operation with the second short-pulse radiation, namely by way of the aforementioned correction member. In order to avoid transverse chromatic aberration as much as possible, it is preferred to arrange the correction member in a pupil of the focusing optics, preferably adapted for pivoting-in. The member can also be configured as an adjustable optical element, in particular as a varifocal lens or a MEMS array, which is activated or deactivated in respect of its corrective effect by the control device which sets the optical element accordingly.

As an alternative to a correction member provided downstream of the beam combiner, it is also possible to embody the beam combiner to contain a correction member with the aforementioned properties, which member only acts on the second short-pulse radiation.

An embodiment with the two input beam paths, in which the first input beam path or the focusing device is corrected to have constant spectral characteristic curves of the longitudinal chromatic aberration in the first wavelength range and in which the second input beam path comprises the correction member, which adapts the characteristic curve of the longitudinal chromatic aberration for the second wavelength range, is particularly preferred due to its structural simplicity. This embodiment allows, in particular, an embodiment of the z-scanner device having a second z-scanner for the second short-pulse radiation in the second input beam path and a first z-scanner for the first short-pulse radiation in the first input beam path. Then, the correction member can be provided directly in the second z-scanner, in particular in a fixed optical member of a telescope, which realizes the second z-scanner in the form of a movable and the fixed optical member.

In one embodiment, the function of the correction member is provided in the already specified refocusing element.

In preferred embodiments, the focusing device is also corrected in respect of monochromatic aberrations for one of the two wavelength ranges and has a residual monochromatic aberration in the other wavelength range. A compensation optics, which compensates the residual monochromatic aberration, is situated in a beam path passed only by the radiation in the other wavelength range. Such structure is particularly advantageous because, once again, an optical design already configured for a given short-pulse radiation can be extended to another short-pulse radiation with little outlay.

In preferred embodiments, compensation optics and correction member and, optionally, refocusing element as well can be combined in one correction optical member.

The centroid wavelength is preferably no more than 420 nm, more preferably between 380 and 420 nm, particularly preferably at 405 nm. The other centroid wavelength is preferably no less than 730 nm, more preferably between 1030 and 1060 nm, particularly preferably at 1040 nm. Each of the two wavelengths can be the first or the second centroid wavelength. Preferably, the two wavelength ranges are each no wider than 30 nm, particularly preferably each no wider than 15 nm.

For applications in corneal surgery, a z-travel of the z-scanner device is preferably at least 1 mm for applications on the cornea that has been pressed flat, further preferably at least 3 mm for applications on the curved cornea, particularly preferably at least 5 mm for work on the lens of the eye and further particularly preferably at least 13 mm for applications in cataract surgery.

Since the z-scanner device comprises a mechanically moving component, which moves a comparatively large travel, arrangement of such components as far away from the patient as possible is preferred in ophthalmological applications. Then, vibrations and noises that could irritate the patient are avoided. It is therefore preferable for the z-scanner device to comprise at least one divergence-varying optical element, which adjustably varies the divergence of the therapy radiation and which is disposed upstream of the xy-scanner. Here, a configuration with a telescope with a stationary converging lens optical unit and a movable lens optical unit is particularly preferred. In embodiments with two z-scanners, one or both z-scanners can be configured in this way. Expediently, the telescope will be configured as a Galilean telescope.

Scanning systems firstly consist of optical components situated upstream of scanning elements in the direction of light. These components are utilized only axially. Secondly, optical components (a focusing device, also referred to as scanning optics), which also image off-axis field beams toward the image, are situated downstream of the scanning elements.

Examples of optical components upstream of scanners are, inter alia, collimators, beam expanders, polarization-optical elements or systems for varying divergence, i.e., for focusing.

Imaging aberrations which are field-independent, i.e., which occur to the same extent both on the optical axis and off the optical axis, may possibly already be corrected by elements upstream of the scanners. These imaging aberrations include, in particular, longitudinal chromatic aberrations and a spherical aberration.

In embodiments, the correction of the system for the two wavelength ranges is carried out as follows:

(i) The scanning optical unit is initially achromatized for one of the two spectral ranges (here, 400 nm to 410 nm) using conventional means according to the prior art and the other aberrations are corrected for the centroid wavelength.

(ii) Further, there are different optical units upstream of the scanning elements for the two wavelength ranges. As a rule, these optical systems are required in two embodiments in any case, since the two light sources often place different demands on the focal length of the collimators or because different divergence variations are required for the different ranges. The two optical systems can be combined at low-loss by way of a dichroic beam splitter upstream of the xy-scanner, for example. As a rule, these optical systems have a simple design due to their exclusive axial paths.

(iii) The scanning optical unit downstream of the xy-scanning element is only partly corrected by the use of exotic special-purpose glasses. The fitting special-purpose glasses are predominantly used in system parts that have a corrective effect on both longitudinal and transverse chromatic aberrations. Here, seen individually, the transverse chromatic aberration is influenced such that the smallest possible changes remain in the considered first wavelength range. In the transverse chromatic aberration diagram, this is expressed by a curve with a infinitesimal gradient. A second zero (apochromatism), i.e., a complete correction of a second wavelength in the conventional sense, is not mandatory. As a result, the outlay in terms of special-purpose glasses is reduced in comparison with the conventional solution. At operation in the other spectral range, the remaining offset between the two wavelength ranges generates a focal distance change or an imaging scale change. This can be compensated by an adapted optics upstream of the xy-scanner (adaptation of the input beam diameter) and by adapting the tilt angle of the xy-scanner and this is immaterial from an application point of view.

(iv) In general, the longitudinal chromatic aberration curve is not corrected, then. Rather, it comprises an offset in the second wavelength range (=focal offset) and a non-vanishing gradient (=primary residual longitudinal chromatic aberration between 1030 nm and 1050 nm). The offset can be corrected by refocusing. According to the invention, this is implemented by an adapted divergence in the optical unit upstream of the xy-scanner. A remaining primary longitudinal chromatic aberration is field-independent and consequently can be compensated by a correction member that is likewise upstream of the xy-scanner, said correction member being situated in the beam path for the second wavelength range only. The operation in the first wavelength range is not impeded thereby since the element is not situated in the beam path in that case. Examples of such a correction member are, inter alia, cemented members (combinations of positive and negative lenses with different types of glass) or diffractive elements.

(v) It is still necessary to correct monochromatic aberrations after correcting the chromatic aberrations for both wavelength ranges. According to (i), this was already implemented by conventional means known from the prior art in the first wavelength range, i.e., by a suitable choice of the lens radii of the scanning optics. However, residual aberrations then remain in the second wavelength range. The remaining spherical aberration (=field independent) can likewise be corrected by a correction element upstream of the xy-scanner. By way of example, this can be an aspherical surface on cemented member according to (iv) or by further spherical lenses of suitable design or by diffractive elements of aspherical effect.

(vi) The correction of the field-dependent monochromatic aberrations can, then, only be done in the optical unit downstream of the xy-scanner. This can be implemented by counterbalancing both spectral ranges, i.e., by a solution which is truly corrected for these aberrations—or whose residual aberrations are acceptable for the application. Where appropriate, aspherical surfaces also can be used in the scanning optics to this end. Formally, this relates to correction of imaging aberrations at two wavelengths (=the two centroid wavelengths), i.e., a conventional and, as a rule, less complicated achromatization. Consequently, the technical outlay is moderate because primary chromatic aberrations for both secondary wavelengths are already compensated. In cases where this solution is not yet satisfactory, it is possible to change parts of the scanning optics for the operation in both spectral ranges where necessary—however, this removes the option of simultaneous using both ranges. This can be implemented by an automated changing system.

(vii) The correction members in the optical unit upstream of the xy-scanner must be provided in an optical plane congruent to the scanning elements, i.e., in a pupil plane. This is the case, in particular, if the system is operated at different focal depths by varying the divergence upstream of the xy-scanner. If the correction members are not located in a pupil plane, the working diameter of the elements changes in different focal positions, and the corrective effect of the elements becomes focus-dependent. According to the invention, this is solved by a 4f relay optics, which is inserted between the divergence-varying element and the xy-scanner. The correction member is then situated in the front focus of the second group of the 4f system and the xy-scanner is situated in the back focus of the first group of the 4f system. The two groups have approximately the spacing of the sum of the two partial focal lengths of the groups (=4f system). This generates mechanical space for inserting the correction elements in the plane congruent to the xy-scanner. Should a plurality of elements have to be introduced, such relay can be stacked multiple times. An embodiment in form of a mirror optical unit (e.g., Offner system) is likewise conceivable.

BRIEF DESCRIPTION OF THE DRAWINGS

The invention is explained in more detail below for example on the basis of the accompanying drawings, which also disclose features essential to the invention. In the figures:

FIG. 8 shows an illustration that is similar to FIG. 5 for a further embodiment of the instrument of FIG. 1, which differs in respect of correction of transverse chromatic aberration.

DETAILED DESCRIPTION

The invention is described below with reference to eye surgery, which should merely represent an example of various tasks in eye therapy for which the various aspects of the invention can be used.

The following examples describe laser-assisted eye surgery using fs-lasers, which are the most frequently employed short-pulse lasers—and hence also the best studied—in the field of laser-assisted eye surgery. Nevertheless, all systems described herein are also implementable using other short-pulse lasers. Therefore, provided the pulse length is not explicitly discussed as a differentiating feature, fs-lasers are used synonymously for short-pulse lasers.

The system described herein, in which the various aspects of the invention are realized purely in exemplary fashion in combination, serves for laser-assisted corneal surgery. Incisions in the cornea are implemented by means of the short-pulse laser beam source, for example for correcting the refractive error. However, the system can also be designed for cataract surgery, e.g., to carry out an access incision to the anterior chamber of the eye through the cornea, a capsulotomy incision, incisions for sectioning the core of the lens of the eye.

Figure 1:
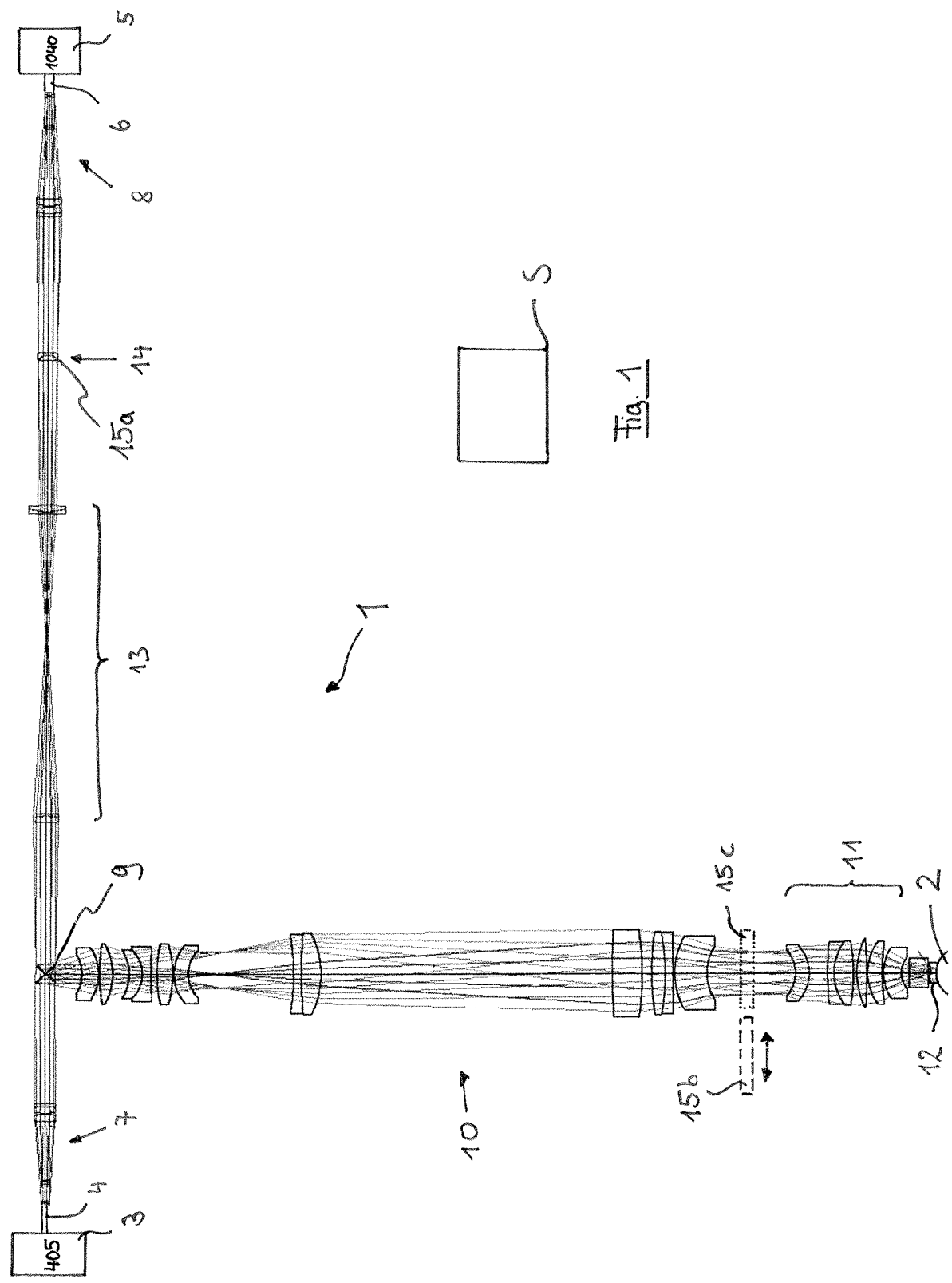
FIG. 1 shows a schematic illustration of an optical unit of an instrument for laser-assisted eye surgery that can operate at two wavelengths, with the beam path illustrated schematically.

FIG. 1 schematically shows the beam path of a therapy system 1 for ophthalmology, in particular for corneal surgery. By producing cut surfaces in the cornea of an eye 2. The therapy system 1 is configured to operate at two wavelengths, namely at a first centroid wavelength of 405 nm and a second centroid wavelength of 1040 nm. The wavelengths are used individually; i.e., the therapy system 1 can be switched between the two wavelengths. In one embodiment of the therapy system 1, a first laser source 3 provides a first laser beam 4 at the first centroid wavelength of 405 nm and a second laser source 5 provides a second laser beam 6 at the second centroid wavelength of 1030 nm. The laser sources 3, 6 are short-pulse laser sources, and so the laser beams 4, 6 are pulsed laser radiation with a pulse length e.g., in the fs range.

A z-scanner 7, which is configured to adjust the depth position of a focus, yet to be explained below, in the cornea of the eye 2, is provided for the first laser beam 4. Equally, the second laser beam 6 is adjusted in terms of focus depth using a second z-scanner 8. An xy-scanner device 9 operates also as a combining element for the two beam paths of the second laser beam 6 and the first laser beam 4 and feeds one of the two laser beams in scanning fashion into the beam path of a focusing optics 10. Selection between the two beams can be implemented by the combiner optical unit provided in the xy-scanner device 9 switching between one of the two beams such that only one of the two beams passes through the focusing optics 10 in scanning fashion. Alternatively, the two beam paths can be combined without switching and only one of the two laser sources 3, 5 is activated. This can be controlled by a control device S, which controls the entire operation of the therapy system 1 and, in particular, also controls the laser sources 3, 5, the xy-scanner device 9 and the z-scanners 7, 8.

The focusing optical unit 10 comprises an objective 11 and focuses the first or second laser beam 4, 6, which was laterally scanned by the xy-scanner device 9, through a contact glass 12 into the cornea of the eye 2.

The two centroid wavelengths differ by more than 500 nm. The focusing in the cornea and the design of the laser sources 3, 5 are configured such that the pulses of the laser beams 4, 6 produce an optical breakdown in the cornea of the eye or separate tissue layers in the cornea of the eye by way of a breakdown-free, nonlinear interaction. A high focus quality needs to be obtained for this effect to occur. In the case of optics designed purely for one of the two wavelengths, the spectral difference between the first and second laser beam 4, 6 would lead to chromatic aberrations occurring at the other wavelength. As a consequence, a desired focal position would no longer be obtained. Moreover, it would no longer be possible to obtain an optical breakdown or nonlinear interaction for that wavelength for which the optics of the therapy system 1 was not designed. Due to the short-pulse nature of the first and second laser radiations 4, 6, the laser beams have a certain bandwidth about the aforementioned centroid wavelengths; i.e., they each cover a wavelength range. Due to physical laws, the width of these wavelength ranges is inseparably linked to the shortness of the laser pulses of the laser beams.

In order to reliably ensure nonlinear interaction in the focus, produced by the focusing optics 10 comprising objective 11, in both modes of operation, i.e., both during operation with the first laser beam 4 and during operation with the second laser beam 6, the therapy system 1 is corrected in a certain way for the first wavelength, i.e., for the radiation of the first laser beam 4, and for the radiation of the second laser beam 6 and the second wavelength range determined thereby. This correction will be explained in more detail below on the basis of FIGS. 5, 6 and 8.

Figure 2:
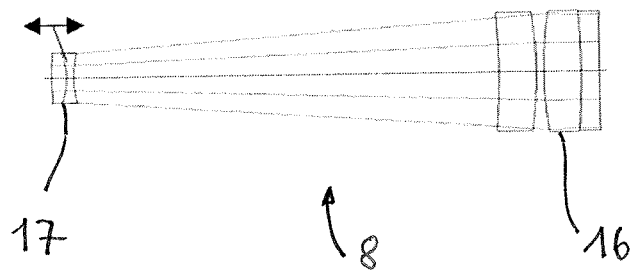
FIG. 2 shows a z-scanner, which is used in the instrument of FIG. 1.

FIG. 2 shows an example of the z-scanner 7 or 8. It is configured as a Galilean telescope with a stationary converging optics 16 and a movable diverging optics 17. The divergence of the radiation downstream of the z-scanner 7, 8 is set appropriately by displacing the movable diverging optics 17, as a result of which it is possible to set the depth position of the focus in the eye 2 together with the focusing optics 10.

Figure 3:
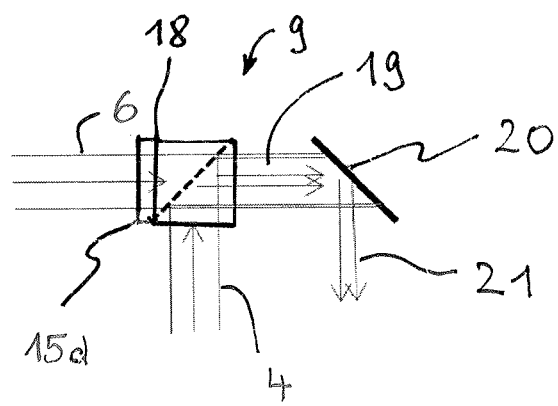
FIG. 3 shows a beam combiner and xy-scanner, which can be used in the instrument of FIG. 1.

FIG. 3 shows a schematic embodiment of the xy-scanner device 9, which comprises a dichroic combiner 18, which combines the second laser beam 6 and the first laser beam 4 and which guides these in a common beam path 19 to a scanner mirror pair 20. There is a scanned beam path 21 from that point, said scanned beam path then passing through the focusing optics 10 and the objective 11 as well as the contact glass 12.

A relay optics 13 is situated downstream of the second z-scanner 8 in the illustration of FIG. 1, and so a pupil plane 14 is created in the beam path between the z-scanner 8 and the xy-scanner device 9. A correction optical member 15a lies in the latter, said correction optical member having a specific function in respect of the color correction of the therapy system 1, which will become clearer below on the basis of FIGS. 5, 6 and 8.

Further FIG. 3 shows a correction optical member 15d which can be provided on the dichroic combiner 12 and which acts on the second laser beam 6. This correction optical member 15d is an alternative to the correction optical member 15a. Its function will also be explained below.

Figure 5:
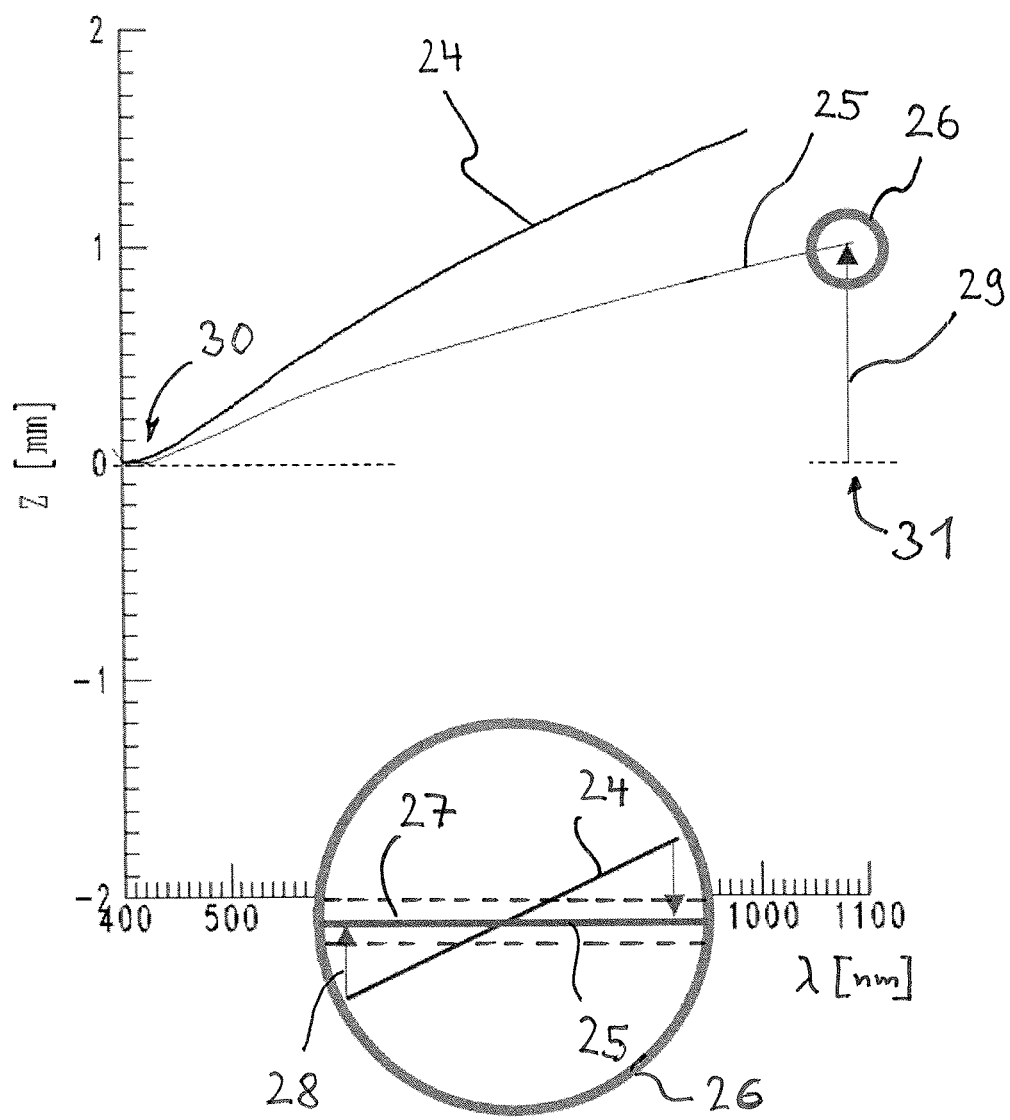
FIG. 5 shows a characteristic curve of longitudinal chromatic aberration of the instrument of FIG. 1.

FIG. 5 shows the spectral curve of the longitudinal chromatic aberration Z of the therapy system 1 in the therapy volume, i.e., in the volume in which the eye 2 is located. The characteristic curve 24 plots the longitudinal chromatic aberration curve against wavelength λ., for a conventional instrument, which is, thus, designed for only one centroid wavelength. As may be seen, the longitudinal chromatic aberration Z increases from a wavelength of 400 nm. There is a longitudinal chromatic aberration between the second centroid wavelength 31, which is 1040 nm in this case, and the first centroid length 31, which is 405 nm in this case. By way of example, this is approximately 1 mm in the illustration of FIG. 5. However, as clarified in the magnification shown at the bottom of the figure, this longitudinal chromatic aberration is largely constant due to a particular correction 28 of the system 1 in the second wavelength range 26 about the second centroid wavelength 31 and said longitudinal chromatic aberration remains within a longitudinal chromatic aberration tolerance 27, which is plotted using dashed lines in the magnified section. Here, the magnified section shows the second wavelength range 26 with a corrected characteristic curve 25. Additionally, the conventional characteristic curve 24 intersects the corrected characteristic curve 25. This emphasises the different gradients. As a result of the particular correction 28 of the system, the characteristic curve 25 is largely horizontal in relation to the uncorrected characteristic curve 24, and so the former characteristic curve remains within the longitudinal chromatic aberration tolerance 27. The characteristic curve 24 does not have this property. Thus, if a system with the characteristic curve 24 is used, it would be possible to exactly compensate the longitudinal chromatic aberration for the second centroid wavelength. However, this requires to use a refocusing that is greater than refocusing 29. This may be tolerable in certain circumstances. However, the problem in that case would be that the characteristic curve would exceed the longitudinal chromatic aberration tolerance 27 in the wavelength range 26 about the second centroid wavelength, which would lead to an axial broadening of the focus. This would no longer be tolerable for applications requiring nonlinear interaction (or, alternatively, for a high-quality eye observation).

It is for this reason that the optics of the therapy system 1 is corrected, i.e., in particular, the focusing optics 10 and the objective 11. Instead of a characteristic curve 24, which still has a gradient in the second wavelength range 26 generating a longitudinal chromatic aberration variation much larger than the longitudinal chromatic aberration tolerance 27, the characteristic curve 25 now extends substantially horizontally. The absolute offset of the longitudinal chromatic aberration is not important in the correction 28. Rather, a longitudinal chromatic aberration is deliberately accepted between the second centroid wavelength 31 and the first centroid wavelength 30. Due to the substantially horizontal curve of the characteristic curve 25—i.e., because the variation in the longitudinal chromatic aberration remains within the longitudinal chromatic aberration tolerance 27 in the second wavelength range 26—it is possible to compensate the longitudinal chromatic aberration present at the second centroid wavelength 31 by simple refocusing 29. The correction 29 does not broaden the focal volume inadmissibly in axial direction, because the correction 29 keeps the characteristic curve 25 constant within the longitudinal chromatic aberration tolerance 27. The axial focus quality remains such that nonlinear interaction is achieved.

To achieve this at both centroid wavelengths 30, 31, the longitudinal chromatic aberration tolerance 27 is also observed in the wavelength range about the first centroid wavelength 31. For simpler illustration, the tolerance is only plotted for the wavelength range 26 about the second centroid wavelength 30 in FIG. 5.

The characteristic curve 25 of the therapy system 1 can be generated in a particularly simple fashion by designing the optics of the therapy system in respect of a conventional longitudinal chromatic aberration correction for the first centroid wavelength 30, i.e., for 405 nm. Then, all that has to be ensured for the second centroid wavelength 31 is that the constancy of the characteristic curve 25 is also given in the wavelength range 26 about the second centroid wavelength 31. This is achieved by the correction optical member 15a-15d, which is passed only by the second laser beam 6 of the second centroid wavelength 31. The configuration of the therapy system 1 with the correction optical member 15a in the pupil plane 14 and in a portion of the beam path prior to the beam combiner at the xy-scanner device 9 is one option for obtaining this correction and constancy of the characteristic curve in the wavelength range 26. Another option is to provide a correction optical member 15b, which is pivoted into a pupil of the common beam path, for example into a pupil of the focusing optical unit 10, when the second laser beam 6 of the second centroid wavelength 31 is active. A further option is to provide an adjustable correction optical member 15c in a pupil that is passed by both beams, said correction optical member being able to be activated and deactivated in respect of its corrective effect. It is switched to a corrective effect when the second laser beam 6 is guided through the system. It is likewise possible to provide the correction optical member at the combiner 18. In this respect, FIG. 3 shows an exemplary of an arrangement of a correction optical member 15d, which only acts on the second laser beam 6.

Figure 4:
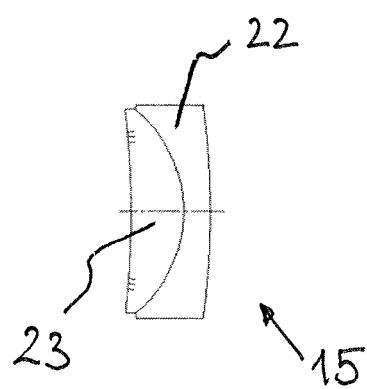
FIG. 4 shows a correction member, which is used for a wavelength in the instrument of FIG. 1.

FIG. 4 shows a possible design for the correction optical member 15a, b, d, comprising a negative optical member 22 and a positive optical member 23. In principle, a person skilled in the art is aware of optical corrections for influencing the longitudinal chromatic aberration characteristic curve.

However, the position of the focus and the extent of the focus is influenced not only by the longitudinal chromatic aberration Z but also by the transverse chromatic aberration F. This is of particular importance in the therapy system 1 since it is a scanning therapy system which laterally adjusts the position of a focus in an image field. Depending on the lateral focus position, the xy-scanner device 9 guides the beams through the focusing optics 10 at different offsets to the optical axis. Naturally, chromatic transverse chromatic aberrations occur at such offsets.

Figure 6:
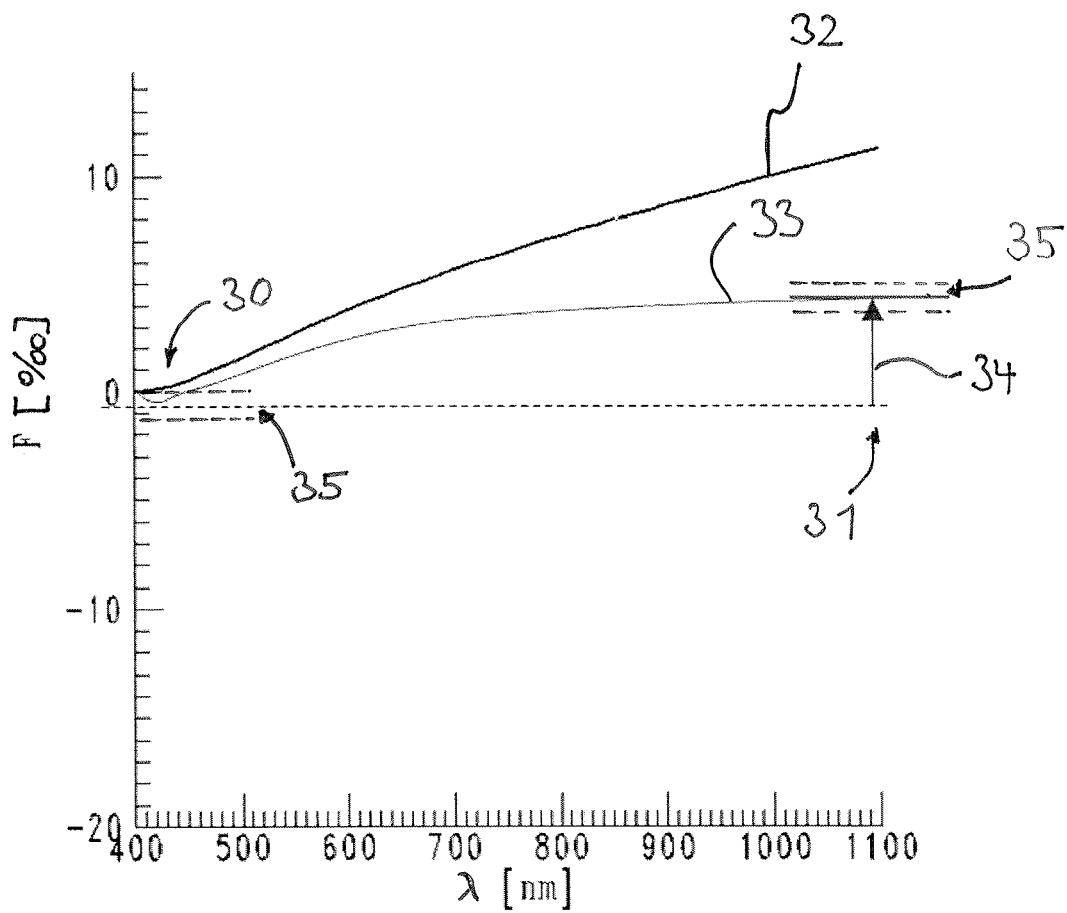
FIG. 6 shows a characteristic curve of transverse chromatic aberration of the instrument of FIG. 1.

FIG. 6 shows the correction of the therapy system 1 and, in particular, of the focusing optical unit 10 provided to address this issue. Plotted here is the spectral curve of the characteristic curve for the transverse chromatic aberration F, which is plotted here in exemplary fashion as a relative transverse chromatic aberration in parts per thousand (‰).

The transverse chromatic aberration 405 is corrected at the first centroid wavelength 30. Consequently, it is a reference wavelength. This would also be the case for a conventional characteristic curve 32. Further, the correction is configured such that a characteristic curve 33 is obtained which is substantially constant at the second centroid wavelength 31. It remains within a transverse chromatic aberration tolerance 35. As a rule, this would not be the case for a correction that is only related to 405 nm. The focusing optics 10 is particularly corrected to obtain such behaviour. The effect of the transverse chromatic aberration present at the second centroid wavelength 31 is that of a deflection angle modification 34. The transverse chromatic aberration can easily be compensated by an appropriately modified actuation of the xy-scanner device 9 when the therapy system 1 operates at the second centroid wavelength 31, i.e., with the second laser beam 6. Since the transverse chromatic aberration remains within the transverse chromatic aberration tolerance 35, even in the second wavelength range, an inadmissible widening of the focal volume in the lateral direction, i.e., transversely to the optical axis, is avoided and reliably nonlinear treatment effects in the tissue continue to be reached in the focus. It is superfluous to mention that the transverse chromatic aberration also remains within the transverse chromatic aberration tolerance 35 at the first centroid wavelength 30. By way of example, the tolerance is 0.5 μm absolute.

The characteristic curve 33 requires no perfect apochromatization of the focusing optics 10. At perfect apochromatization, the transverse chromatic aberration would also disappear around the second centroid wavelength 31. Since this is not demanded, but only that the transverse chromatic aberration must remain within the transverse chromatic aberration tolerance both in the second wavelength range that surrounds the second centroid wavelength 31 and in the first wavelength range that surrounds the first centroid wavelength 30, the optical correction is simplified.

Figure 7:
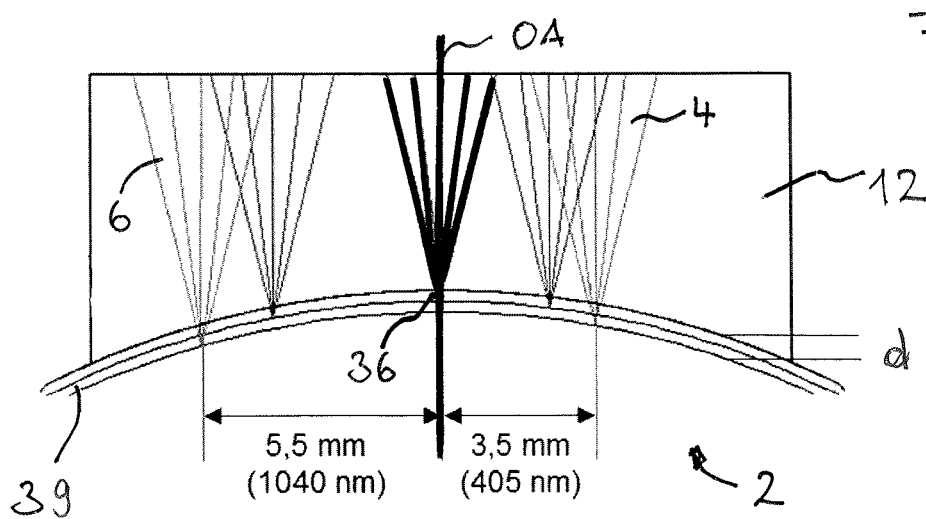
FIG. 7 shows a magnified illustration of focusing therapy radiation in a cornea of the eye.

FIG. 7 shows the effect on the position of a focus 36 in the cornea 39 of the eye 2. The transverse chromatic aberration F has no effect in the case of incidence on the optical axis OA. It only plays a role once the focus 36 is deflected laterally in the cornea 39. For a given deflection by the scanner mirror 20, different lateral displacements of the focus 36 arise depending on the wavelength. The two beams on the left show the conditions for the second laser beam 6 at the second centroid wavelength 31, the two beams on the right show the conditions for the first laser beam 4 at the first centroid wavelength 30. It may be seen that there is a different lateral displacement of the focus 36 in the cornea 39 for the same deflection angle by the scanner mirror 20. This sets-in due to the transverse chromatic aberration present at the second centroid wavelength 31. This difference is compensated by the control device S by way of a suitable deflection angle modification 36, and so the focus 36 once again lies at a desired point in the cornea.

FIG. 7 further shows the meaning of refocusing for the purposes of compensating the longitudinal chromatic aberration. The thickness d of the cornea is 0.5 mm. Without refocusing, the longitudinal chromatic aberration between second and first centroid wavelength 31, 30 would have a value of 1 mm. This value would be greater than thickness d of the cornea 39, and so the focus 36 at one of the two wavelengths would lie completely outside of the cornea 39 which is unwanted. This is prevented by the refocusing 29. The refocusing 29 is obtained by an appropriate configuration of the control device S, which provides control of the z-scanner 7, 8 with an offset in order to effect the refocusing 29 and in order to compensate for the longitudinal chromatic aberration. As an alternative or in addition thereto, use can be made of a corresponding optical member, which modifies the axial position. In embodiments, this optical member can be combined with, or provided in, the correction optical member 15a-d.

FIGS. 5 and 6 show conditions in which the longitudinal chromatic aberration or the transverse chromatic aberration is corrected for one wavelength, for the first centroid wavelength 30 in the shown embodiments. The first centroid wavelength therefore is the reference wavelength mentioned above. However, this is not mandatory. Characteristic curves 25, 33, which have a longitudinal chromatic aberration Z and/or a transverse chromatic aberration F that differs from zero at both centroid wavelengths 30, 31, i.e., that have a completely different reference wavelength, are also possible. This is completely harmless for as long as the corresponding aberrations do not exceed the prescribed aberration tolerance ranges in the corresponding wavelength ranges about the centroid wavelengths 30, 31.

FIG. 8 shows a configuration in respect of the transverse chromatic aberration F that is corresponding in exemplary fashion. Here, the latter is zero at the second centroid wavelength 31 and differs from zero at the first centroid wavelength 30. However, care is once again taken to ensure that the transverse chromatic aberration does not exceed the transverse chromatic aberration tolerance 35 within the wavelength ranges, which are indicated by numerals 37 and 38.

Thus, in principle, the correction of the therapy system 1 is designed such that both the longitudinal chromatic aberration and the transverse chromatic aberration have local extremata in the wavelength ranges arising around the centroid wavelengths 30, 31 due to the pulse length, said extremata having such a flat shape that the corresponding tolerances are not exceeded in the wavelength ranges and, hence, nonlinear interaction in the focus occurs reliably. As a result, the correction is very much easier than if vanishing longitudinal chromatic aberrations and transverse chromatic aberrations were to be demanded at both centroid wavelengths 30, 31 and within the wavelength ranges surrounding these.

Ultimately, setting the zero in respect of the longitudinal chromatic aberration is a scaling. It is possible in each curve to define the z-value at one of the two centroid wavelengths as a reference plane, i.e., as a zero plane, of the focal depth specification. Ultimately, from a physical point of view, the longitudinal chromatic aberration is only, of course, a change in the focal plane when changing between two wavelengths, the centroid wavelengths 30, 31 in this case.

In addition to chromatic aberrations, each imaging system also has monochromatic aberrations. Here, in embodiment c, the therapy system is designed such that the monochromatic aberrations are only compensated for one of the two wavelengths for the beam path from the laser source to the eye. For the other wavelength, a compensation element is inserted into the part of the beam path that is passed only by this wavelength, or a compensation element is pivoted into the common beam path when the other wavelength is active or an adjustable compensation element in the common beam path is activated or suitably set when the other wavelength is active. In a particularly expedient embodiment, the compensation element is combined with the correction optical member.

The invention claimed is:

1. A system for therapy or measurement of the eye by treating tissue using nonlinear interaction with therapy or measurement radiation, the system comprising:
   a laser device, which provides the therapy or measurement radiation,
   a focusing device, including an objective lens, which comprises an image field lying in a therapy or measurement volume and which focuses the therapy or measurement radiation onto a focus in the image field such that the treatment or measurement is producible within the tissue using nonlinear interaction,
   an xy-scanner device, disposed upstream of the focusing device, for lateral displacement of the focus in the image field,
   a z-scanner device, including a moveable lens, which adjusts a depth position of the focus in the therapy or measurement volume, and
   a control device, which controls the xy-scanner device and the z-scanner device,
   wherein
   the laser device provides, as the therapy or measurement radiation, a first short-pulse radiation at a first centroid wavelength and a second short-pulse radiation at a second centroid wavelength, which differs from the first centroid wavelength by at least 300 nm, wherein the first short-pulse radiation covers a first wavelength range about the first centroid wavelength due to a pulse length of the first short-pulse radiation and the second short-pulse radiation covers a second wavelength range about the second centroid wavelength due to a pulse length of the second short-pulse radiation, wherein
   the system is configured to operate with the first short-pulse radiation and the second short-pulse radiation, but not simultaneously with both the first short-pulse radiation and the second short-pulse radiation,
   wherein optics of the system, including the objective lens of the focusing device, and the moveable lens of the z-scanner device, are configured to produce a longitudinal chromatic aberration at at least one of the two centroid wavelengths, wherein in both wavelength ranges the longitudinal chromatic aberration remains within an upper longitudinal chromatic aberration limit and a lower longitudinal chromatic aberration limit over the wavelength range, the upper and lower longitudinal chromatic aberration limits being constant over the wavelength range and being determined by a predetermined longitudinal chromatic aberration tolerance,
   wherein the optics of the system, including the objective lens of the focusing device and the moveable lens of the z-scanner device, are also configured to produce a transverse chromatic aberration at at least one of the two centroid wavelengths, wherein in both wavelength ranges the transverse chromatic aberration remains within an upper transverse chromatic aberration limit and a lower transverse chromatic aberration limit over the wavelength range, the upper and lower transverse chromatic aberration limits being constant over the wavelength range and being determined by a predetermined transverse chromatic aberration tolerance, and wherein the control device is configured to control the xy-scanner device such that the transverse chromatic aberration is compensated for by a deflection function for the lateral displacement of the focus.

2. The system as claimed in claim 1, wherein a wavelength in the first wavelength range is used as a reference wavelength for the longitudinal chromatic aberration and the control device is configured to control the z-scanner device such that, during operation with the second short-pulse radiation, the longitudinal chromatic aberration is compensated by a depth position offset of the focus by adjusting a position of the moveable lens of the z-scanner device.

3. The system as claimed in claim 1, wherein a wavelength in the first wavelength range is used as a reference wavelength for the longitudinal chromatic aberration and the system comprises a refocusing lens, which only acts on the second short-pulse radiation or which is only activated during operation with the second short-pulse radiation, said refocusing lens compensating the longitudinal chromatic aberration by a depth position offset of the focus.

4. The system as claimed in claim 1, comprising a refocusing lens, which only acts on the second short-pulse radiation or which is only activated during operation with the second short-pulse radiation, said refocusing lens causing the characteristic curve of the longitudinal chromatic aberration in the second wavelength range to be constant within the longitudinal chromatic aberration tolerance.

5. The system as claimed in claim 1, comprising a first input beam path for the first short-pulse radiation and a second input beam path for the second short-pulse radiation, and a beam combiner disposed upstream of the focusing device, said beam combiner merging the two input beam paths or switching between the two input beam paths, wherein the first input beam path and the focusing device together affect characteristics of the longitudinal chromatic aberration, such that the longitudinal chromatic aberration is within the upper and lower longitudinal chromatic aberration limits over the first wavelength range, wherein a correction lens that is controlled by the control device is disposed downstream of the beam combiner in the beam path, said correction lens being selectively activatable by the control device to produce or cease a corrective effect and said correction lens modifying the characteristics of the longitudinal chromatic aberration, such that the longitudinal chromatic aberration in the second wavelength range is within the upper and lower longitudinal chromatic aberration limits over the second wavelength range while the correction lens is activated to produce the corrective effect, and wherein the control device is configured to activate the correction lens to produce the corrective effect when the second short-pulse radiation passes through the system, and to deactivate the correction lens to cease the corrective effect when the first short-pulse radiation passes through the system.

6. The system as claimed in claim 5, wherein the focusing device is disposed downstream of the xy-scanner device and the correction lens is switchable, preferably pivotable, into and out of a pupil of the focusing device.

7. The system as claimed in claim 5, wherein the focusing lens is disposed downstream of the xy-scanner device and the correction lens is arranged in a pupil of the focusing lens and embodied as an adjustable optical element, in particular as a varifocal lens or a microelectromechanical systems (MEMS) array.

8. The system as claimed in claim 1, comprising a first input beam path for the first short-pulse radiation and a second input beam path for the second short-pulse radiation and a beam combiner disposed upstream of the focusing device, said beam combiner merging the two input beam paths or switching between the two input beam paths, wherein the first input beam path and the focusing device affect characteristics of the longitudinal chromatic aberration, such that the longitudinal chromatic aberration is within the upper and lower longitudinal chromatic aberration limits over the first wavelength range, wherein the beam combiner comprises a correction lens, which only acts on the second short-pulse radiation and which modifies the characteristics of the longitudinal chromatic aberration to be within the upper and the lower longitudinal chromatic aberration limits over the second wavelength range.

9. The system as claimed in claim 1, comprising a first input beam path for the first short-pulse radiation and a second input beam path for the second short-pulse radiation and a beam combiner disposed upstream of the focusing device, said beam combiner merging the two input beam paths or switching between the two input beam paths, wherein the first input beam path and the focusing device together affect characteristics of the longitudinal chromatic, such that the longitudinal chromatic aberration is within the upper and lower longitudinal chromatic aberration limits over the first wavelength range, and wherein the second input beam path comprises a correction lens, which modifies the characteristics of the longitudinal chromatic aberration to be within the upper and the lower longitudinal chromatic aberration limits over the second wavelength range.

10. The system as claimed in claim 9, wherein the z-scanner device comprises a second z-scanner for the second short-pulse radiation, which second z-scanner is arranged in the second input beam path, and a first z-scanner for the first short-pulse radiation, which first z-scanner is arranged in the first input beam path, wherein the correction lens is arranged in the second z-scanner.

11. The system as claimed in claim 10, wherein the second z-scanner is configured as a telescope with a movable and a fixed optical lens, wherein the fixed optical lens is configured also as the correction lens.

12. The system as claimed claim 3, wherein the correction lens is configured also as the refocusing lens.

13. The system as claimed in claim 1, wherein the focusing device is corrected with respect to monochromatic aberrations for one of the two wavelength ranges and said focusing device has a residual monochromatic aberration in the other wavelength range and compensation optics, which compensate for the residual monochromatic aberration, are arranged in a beam path passed only by the radiation in the other wavelength range.

14. The system as claimed in claim 5, wherein the focusing device is corrected with respect to monochromatic aberrations for one of the two wavelength ranges and said focusing device has a residual monochromatic aberration in the other wavelength range and compensation optics, which compensate for the residual monochromatic aberration, is arranged in a beam path passed only by the radiation in the other wavelength range, and wherein the correction lens and the compensation optics are combined to form a correction optical member.

15. The system as claimed in claim 1, wherein one of the two centroid wavelengths is not greater than 420 nm, and the other of the two centroid wavelengths is not less than 730 nm.

16. The system as claimed in claim 1, wherein the two wavelength ranges are each no wider than 30 nm.

17. The system as claimed in claim 1, wherein a z-travel of the focus of the z-scanner device is at least 1 mm.

18. The system as claimed in claim 15, wherein one of the two centroid wavelengths is between 380 and 420 nm and the other of the two wavelengths is between 1030 nm and 1060 nm.

19. The system as claimed in claim 16, wherein the two wavelength ranges are no wider than 15 nm.

20. The system as claimed in claim 17, wherein the z-travel of the focus of the z-scanner device is at least 13 mm.

* * * * *